United States Patent
Edwards et al.

(10) Patent No.: US 9,645,277 B2
(45) Date of Patent: May 9, 2017

(54) ESTIMATING MOLECULAR SIZE DISTRIBUTIONS IN FORMATION FLUID SAMPLES USING A DOWNHOLE NMR FLUID ANALYZER

(71) Applicants: Carl M. Edwards, Katy, TX (US);
Jinhong Chen, Katy, TX (US)

(72) Inventors: Carl M. Edwards, Katy, TX (US);
Jinhong Chen, Katy, TX (US)

(73) Assignee: BAKER HUGHES INCORPORATED, Houston, TX (US)

( * ) Notice: Subject to any disclaimer, the term of this patent is extended or adjusted under 35 U.S.C. 154(b) by 1124 days.

(21) Appl. No.: 13/765,414

(22) Filed: Feb. 12, 2013

(65) Prior Publication Data

US 2014/0225607 A1   Aug. 14, 2014

(51) Int. Cl.
*G01V 3/00* (2006.01)
*G01V 3/32* (2006.01)
*G01R 33/20* (2006.01)
*G01N 24/08* (2006.01)

(52) U.S. Cl.
CPC ............ *G01V 3/32* (2013.01); *G01N 24/081* (2013.01); *G01R 33/20* (2013.01)

(58) Field of Classification Search
CPC ....................................................... G01R 33/20
USPC ........................................ 324/307, 309, 303
See application file for complete search history.

(56) References Cited

U.S. PATENT DOCUMENTS

| | | |
|---|---|---|
| 5,698,979 A | 12/1997 | Taicher et al. |
| 6,111,408 A | 8/2000 | Blades et al. |
| 6,111,409 A | 8/2000 | Edwards et al. |
| 6,346,813 B1 | 2/2002 | Kleinberg |
| 6,737,864 B2 | 5/2004 | Prammer et al. |
| 6,825,657 B2 | 11/2004 | Kleinberg et al. |
| 6,841,996 B2 | 1/2005 | Madio et al. |
| 6,859,032 B2 | 2/2005 | Heaton et al. |

(Continued)

OTHER PUBLICATIONS

Notification of Transmittal of the International Search Report and the Written Opinion of the International Searching Authority, or the Declaration; PCT/US2014/015700; Nov. 20, 2014, 15 pages.

(Continued)

*Primary Examiner* — Louis Arana
(74) *Attorney, Agent, or Firm* — Cantor Colburn LLP (57) ABSTRACT

A method for estimating a property of subsurface material includes extracting a sample of the material using a downhole formation tester and performing a plurality of nuclear magnetic resonance (NMR) measurements on a sensitive volume in the sample where each measurement in the plurality is performed in a static homogeneous magnetic field with a pulsed magnetic field gradient that is different in magnitude from other NMR measurements to provide a waveform signal. The method further includes transforming each received waveform signal from a time domain into a frequency domain and comparing the frequency domain signal to a reference to provide proton chemical-shift information related to a chemical property of one or more molecules in the sample and transforming the frequency domain signals into a complex number domain that quantifies waveform signal amplitude changes to provide one or more diffusion rates with each diffusion rate being associated with a corresponding frequency.

18 Claims, 8 Drawing Sheets

(56) References Cited

U.S. PATENT DOCUMENTS

| | | | |
|---|---|---|---|
| 6,859,034 B2* | 2/2005 | Chen | G01V 3/32 |
| | | | 324/303 |
| 6,891,369 B2 | 5/2005 | Hurlimann et al. | |
| 6,958,604 B2 | 10/2005 | An et al. | |
| 7,053,611 B2 | 5/2006 | Freedman | |
| 7,301,339 B1 | 11/2007 | Cheng et al. | |
| 7,372,264 B2 | 5/2008 | Akkurt et al. | |
| 7,511,487 B2 | 3/2009 | Badry et al. | |
| 7,667,462 B2 | 2/2010 | Song et al. | |
| 7,683,613 B2 | 3/2010 | Freedman et al. | |
| 2003/0006768 A1 | 1/2003 | Kleinberg et al. | |
| 2003/0214287 A1 | 11/2003 | Sun et al. | |
| 2004/0130324 A1 | 7/2004 | Edwards | |
| 2008/0150524 A1 | 6/2008 | Song et al. | |
| 2008/0150525 A1* | 6/2008 | Song | G01N 24/08 |
| | | | 324/307 |
| 2009/0105955 A1 | 4/2009 | Castillo et al. | |
| 2009/0219019 A1 | 9/2009 | Taherian et al. | |
| 2010/0315081 A1 | 12/2010 | Chanpura et al. | |
| 2012/0169334 A1 | 7/2012 | Hopper et al. | |
| 2015/0192011 A1* | 7/2015 | Mandal | E21B 49/087 |
| | | | 324/303 |
| 2016/0003753 A1* | 1/2016 | Augustine | G01N 24/084 |
| | | | 324/309 |

OTHER PUBLICATIONS

Botana, A., et al. "High resolution 13C DOSY: The DEPTSE experiment." Journal of Magnetic Resonance 211 (2011) (1): 25-29.
Chen, et al. "Characterization of Pore Structures Using NMR-Restricted Diffusion Measurements" SPE 24812 67th Annual Technical Conference and Exhibition, Oct. 4-7, 1992.
Danieli, et al. Small Magnets for Portable NMR Spectrometers. Angew. Chem. Int. Ed. 2010, 49, 4133-4135.
Diffusion NMR. (retrieved on Dec. 13, 2012 (Dec. 13, 2012)]. Retrieved from the internet:,URL:http://chem.ch.huji.ac.il/nmr/techniques/other/diff/diff.html.
Durand, E., et al. (2008). "1H Diffusion-Ordered Spectroscopy (DOSY) Nuclear Magnetic Resonance (NMR) as a Powerful Tool for the Analysis of Hydrocarbon Mixtures and Asphaltenes." Energy & Fuels 22(4): 2604-2610.
Freedman, "Field Applicatons of a New Nuclear Magnetic Resonance Fluid Characterization Method", SPE 71713 Annual Technical Conference and Exhibition, Sep. 30-Oct. 3, 2001, New Orleans, Louisiana. 12 Pages.
Harbe, et al., Principles and limitations of NMR diffusion measurements Journal of Medical Physics, Jan.-Mar. 2007. (Jan.-Mar. 2007) [retrieved on Dec. 13, 2012 (Dec. 13, 2012)]. Retrieved from the internet:,URL:http://www.ncbi. nlm.nih.gov/pmc/articles/PMC3003887/.
Johnson Jr., "Diffusion ordered nuclear magnetic resonance spectroscopy: principles and applications" Progress in Nuclear Magnetic Resonance Spectroscopy 34 (1999), 203-256.
Kapur, G. S., et al. (2000). "Analysis of hydrocarbon mixtures by diffusion-ordered NMR spectroscopy." Fuel 79(11): 1347-1351.
Morris, K. F. and C. S. Johnson (1993). "Resolution of discrete and continuous molecular size distributions by means of diffusion-ordered 2D NMR spectroscopy." Journal of the American Chemical Society 115: 4291-4299.
Novoa-Carballal, R., E. Fernandez-Megia, et al. (2011). "NMR methods for unravelling the spectra of complex mixtures." Natural Product Reports 28(1): 78-98.
Price, "Pulsed-Field Gradient Nuclear Magnetic Resonance as a Tool for Studying Translational Diffusion: Part 1. Basic Theory". Water Research Institute, Sengen 2-1-6, Tsukuba, Ibaraki 305 Japan. Received Jul. 18, 1996, revised May 5, 1997 and accepted May 9, 1997. John Wiley and Sons, Inc. pp. 299-336.
Silva, et al. "Chromatographic and spectroscopic analysis of heavy crude oil mixtures with emphasis in nuclear magnetic resonance spectroscopy", Analytica Chimica Acta vol. 707, Issues 1-2, Nov. 30, 2011, pp. 18-37.
Sun, et al. "T1MAS 2D NMR Technique Provides Valuable Information on Produced Oil", 2003. Society of Petrophysicists and Well Log Analysts. SPWLA 44th Annual Logging Symposium, Jun. 22-25, 2003.
Topspin, "DOSY and Diffusionby NMR". Bruker Biospin. A tutorial for Top spin 2.0. 32 pages.

* cited by examiner

ESTIMATING MOLECULAR SIZE DISTRIBUTIONS IN FORMATION FLUID SAMPLES USING A DOWNHOLE NMR FLUID ANALYZER

BACKGROUND

Hydrocarbon exploration can be very expensive. In order to lower the risk of investment and efficiently use drilling and production resources, it is important to know the types of hydrocarbons that may be present in a reservoir in an earth formation.

One way to determine the types of hydrocarbons that may be present in a formation is to convey a measurement instrument or downhole tool through a borehole penetrating the formation. The tool can then perform measurements from the borehole, which a petro-analyst can analyze to estimate the types of hydrocarbons.

There are many types of hydrocarbons that may be present in the formation. Some of them may have chemical characteristics that may be similar to the characteristics of other types of hydrocarbons leading to data that may be difficult to analyze or to data that may present a false indication. Hence, it would be appreciated in the drilling and geo-physical exploration industries if drilling instruments and tools could be developed to more accurately characterize hydrocarbons in earth formations.

BRIEF SUMMARY

Disclosed is a method for estimating a property of subsurface material. The method includes conveying a carrier through a borehole penetrating the subsurface material and extracting a sample of the subsurface material using a formation tester disposed at the carrier. The method further includes performing a plurality of nuclear magnetic resonance (NMR) measurements on a sensitive volume in the sample using an NMR instrument where each measurement in the plurality of NMR measurements provides an electromagnetic waveform signal received with an antenna. Each NMR measurement in the plurality of NMR measurements is performed (a) in a static homogeneous magnetic field, (b) with a sequence of pulses of radio-frequency (RF) electromagnetic energy transmitted from a transmitter antenna, and (c) with a series of pulsed magnetic field gradients being applied to the sample where the series is superimposed over the static homogeneous magnetic field and has a magnitude that is different from the magnitude in other NMR measurements. The method further includes transforming each received waveform signal from a time domain into a frequency domain to provide a frequency domain signal that is a function of frequency and comparing the frequency domain signal to a reference to provide proton chemical-shift information related to a chemical property of one or more molecules in the sample. The method further includes transforming the frequency domain signals having the same frequency as a function of the magnitude of the pulsed field gradient into a complex number domain that quantifies waveform signal amplitude changes to provide one or more diffusion rates with each diffusion rate being associated with a corresponding frequency and estimating the property using the proton chemical-shift information and the one or more diffusion rates.

Also disclosed is an apparatus for estimating a property of a subsurface material. The apparatus includes a carrier configured to be conveyed through a borehole penetrating the subsurface material, a formation tester disposed at the carrier and configured to extract a sample of the subsurface material, a nuclear magnetic resonance (NMR) instrument disposed at the carrier, and a processor. The nuclear magnetic resonance (NMR) instrument is configured to perform a plurality of nuclear magnetic resonance (NMR) measurements on a sensitive volume in the sample where each measurement in the plurality of NMR measurements provides an electromagnetic waveform signal and each NMR measurement in the plurality of NMR measurements is performed (a) in a static homogeneous magnetic field, (b) with a sequence of pulses of radio-frequency (RF) electromagnetic energy transmitted from a transmitter antenna, and (c) with a series of pulsed magnetic field gradients being applied to the sample. The series of pulsed magnetic field gradients is superimposed over the static homogeneous magnetic field and has a magnitude that is different from the magnitude in other NMR measurements. The NMR instrument includes: a magnetic field source configured to apply the homogeneous magnetic field to the sensitive volume; a transmitter antenna configured to transmit a radio-frequency (RF) signal into the sensitive volume; a pulsed magnetic field gradient source configured to apply the series of pulsed magnetic field gradients with various magnitudes to the sensitive volume; a receiver antenna configured to receive the electromagnetic waveform signals from the sensitive volume due the RF signal and the pulsed magnetic field gradient. The processor is configured to: receive each of the electromagnetic waveform signals; transform each received waveform signal from a time domain into a frequency domain to provide a plurality of frequency domain signals and compare the frequency domain signals to a reference to provide proton chemical-shift information related to a chemical structure of one or more molecules in the sample; transform the frequency domain signals at the same frequency as a function of the magnitude of the pulsed field gradient into a complex number domain that quantifies waveform signal amplitude changes to provide one or more diffusion rates with each diffusion rate being associated with a corresponding frequency; and estimate the property using the proton chemical-shift information and the one or more diffusion rates.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments of the disclosed apparatus and method presented herein by way of exemplification and not limitation with reference to the Figures.

Disclosed are method and apparatus for estimating a molecular chemical composition and a molecular size of hydrocarbons in an earth formation using a downhole nuclear magnetic resonance (NMR) instrument. A set of NMR measurements are performed downhole on a sample of the hydrocarbons and from the measurement set the molecular chemical composition and size are determined. Because different hydrocarbon types may have a similar chemical composition, the molecular size determination is used to differentiate between the different types of hydrocarbons.

Figure 1:
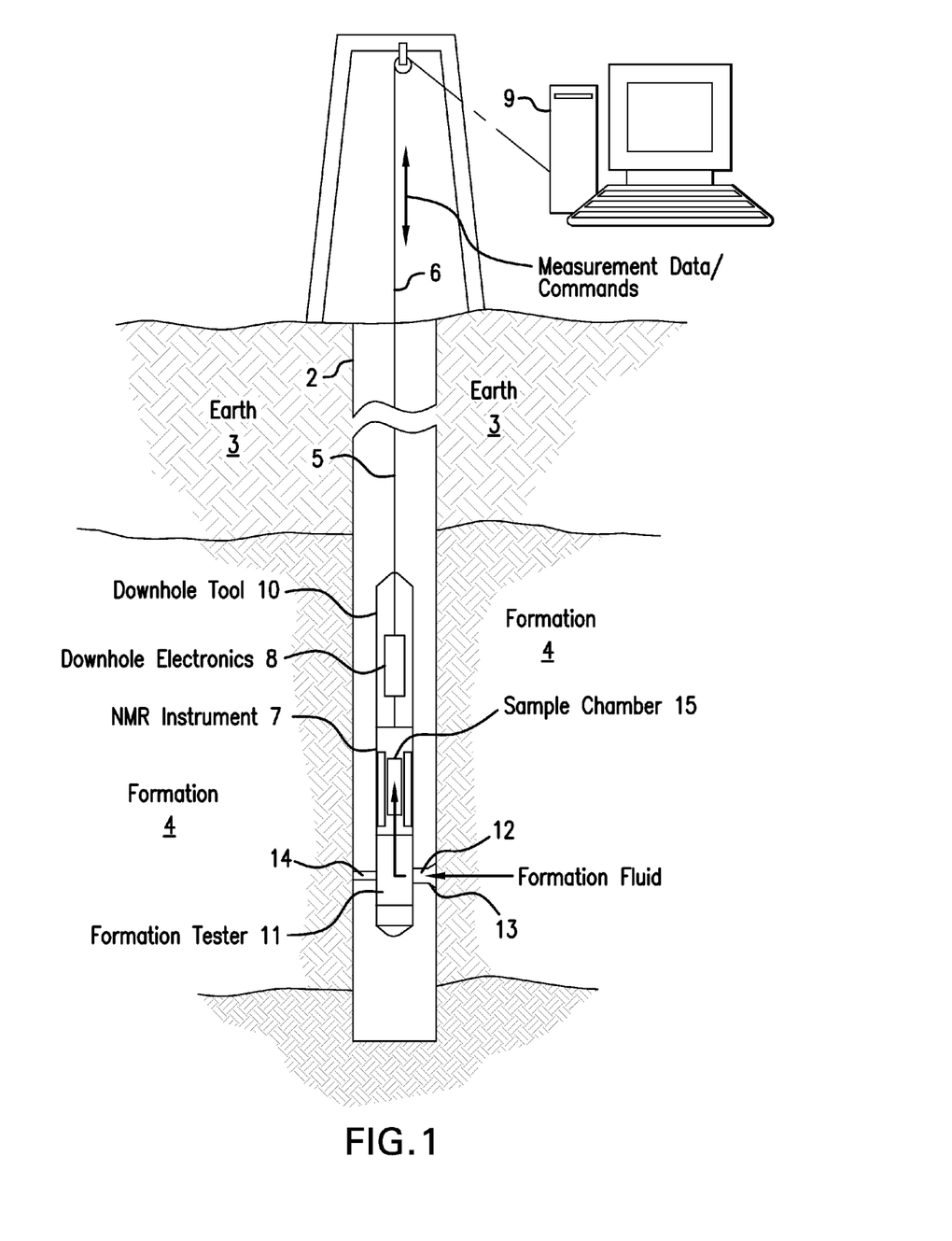
FIG. 1 illustrates a cross-sectional view of an exemplary embodiment of a nuclear magnetic resonance (NMR) downhole tool disposed in a borehole penetrating the earth.

FIG. 1 illustrates a cross-sectional view of an exemplary embodiment of a downhole tool 10 disposed in a borehole 2 penetrating the earth 3, which includes an earth formation 4. The term "subsurface material" may be used to refer to any material below the surface of the earth 3, such as the formation 4, a formation fluid or solid, and a borehole material, as non-limiting examples. The downhole tool 10 is conveyed through the borehole 2 by a carrier 5. In the embodiment of FIG. 1, the carrier 5 is an armored wireline 6. Besides supporting the downhole tool 10, the wireline 6 can provide communications (i.e., telemetry) between the downhole tool 10 and a computer processing system 9 disposed at the surface of the earth 3. Communications can include sending measurements uphole to the computer processing system 9 or commands downhole to the downhole tool 10. In order to operate the downhole tool 10, process measurement data, and/or provide a communications interface with the surface computer processing system 9, the downhole tool 10 includes downhole electronics 8. The operating, processing, and display functions of the disclosure may be performed by the downhole electronics 8, the computer processing system 9, or a combination thereof. In an alternative embodiment referred to as logging-while-drilling (LWD) or measurement-while-drilling (MWD), the carrier 5 can be a drill string or drill tubular. In wireline, LWD, or MWD embodiments, measurement data may be downloaded in real time or after the downhole NMR tool 10 is retrieved from the borehole 2.

In order to extract a sample of a subsurface material, the downhole tool 10 includes a formation tester 11. The formation tester 11 includes a probe 12 configured to extend from the formation tester 11 and seal to a wall of the borehole 2. The sealing may be performed using a pliable pad 13 disposed at the end of the probe 12. A brace 14 may be extended to brace the tool 10 while the probe 12 is sealed to the borehole wall. The formation tester 11 is configured to extract a sample of the subsurface material of interest through the probe 12 and deposit the sample in an NMR sample chamber 15 configured to contain the sample for NMR testing by an NMR instrument 7.

Figure 2:
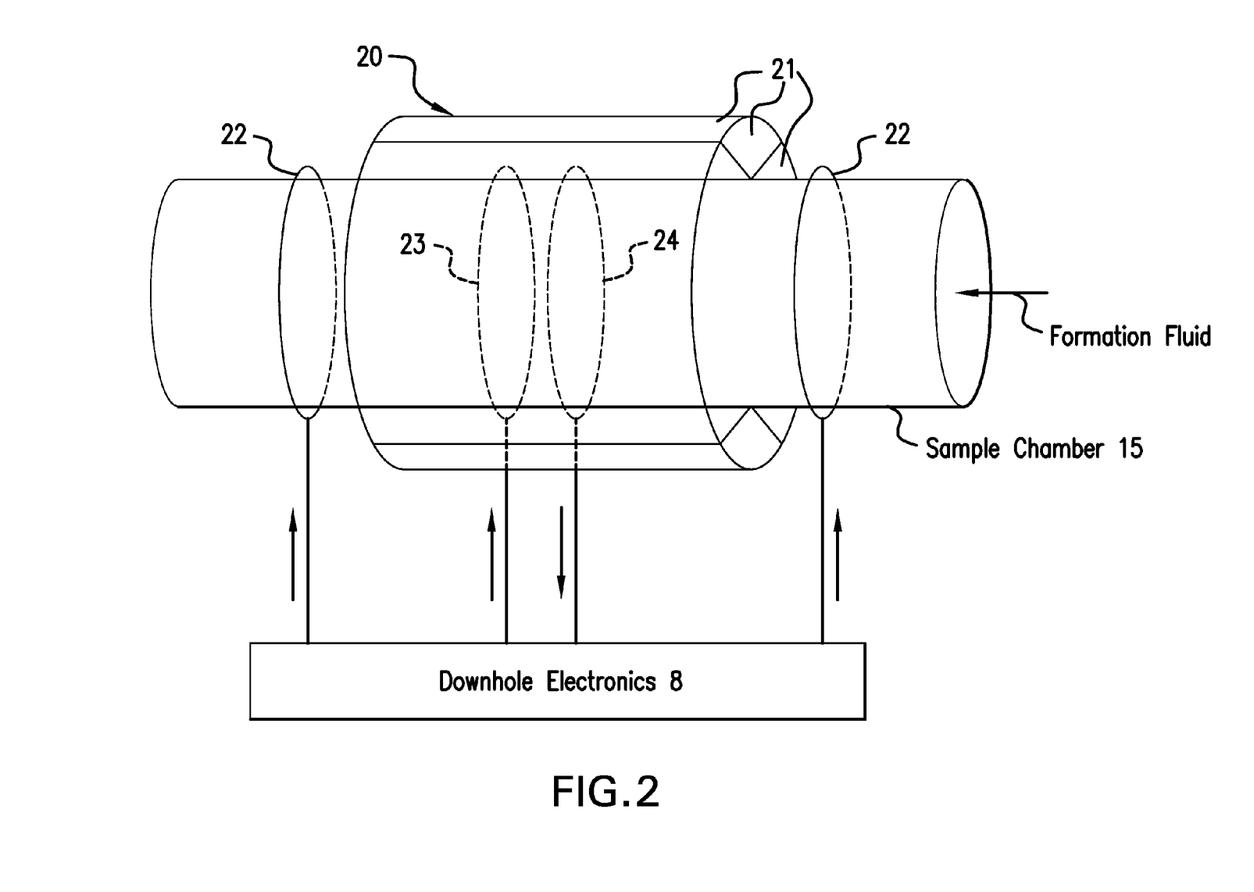
FIG. 2 depicts aspects of the NMR downhole tool.

Reference may now be had to FIG. 2 depicting aspects of the NMR instrument 7 in a side view. The NMR instrument 7 is configured to perform NMR experiments or measurements on the subsurface material sample in the sample chamber 15. Several types of NMR measurements involving a static magnetic field and radio-frequency pulses may be performed on the sample. The various NMR measurements all involve applying a homogeneous magnetic field to a NMR sensitive volume in the sample chamber 15. The term "homogeneous magnetic field" relates to a magnetic field having a variation of magnitude in the sensitive volume that is less than 5 parts per million (ppm) over the NMR sensitive volume in which the NMR measurements are performed. In one or more embodiments, the variation is less than 1 ppm. The static homogeneous magnetic field has a static direction and static homogeneous magnitude, which enable proton chemical shift measurements. In order to apply the homogeneous magnetic field, the NMR instrument 7 includes a magnetic field source 20. In one or more embodiments, the magnetic field source 20 includes an array of magnets 21, such as a Halbach array, which is configured to provide a uniform (i.e., homogeneous) magnetic field inside of the sample chamber 15. It can be appreciated that increasing the number of magnets or changing their positions or orientations in the array of magnets 21 or adding additional magnetic materials may increase the uniformity of the magnetic field.

The NMR measurements include applying RF electromagnetic energy to the sample using a transmitter antenna 22, which may be a conductive coil. It can be appreciated that various pulse sequences may be used in the NMR measurements. In one or more embodiments, a first pulse of RF energy may be applied to orient the magnetic moments or spins of protons in the sample 90° with respect to the static magnetic field followed by a second pulse of RF energy to shift the magnetic moments or spins of the protons 180° with respect to their previous orientation.

Following each RF pulse, a pulsed magnetic field gradient is superimposed on the static homogeneous magnetic field in the sensitive volume by a pulsed magnetic field gradient source 23, which may be a conductive coil. Following the last RF pulse, a resulting electromagnetic waveform (also referred to as a spin echo, or NMR signals) due to precession of the proton magnetic spins is received by a receiver antenna 24, which may be a conductive coil. In general, the waveform is in the time domain and has an alternating form (e.g. alternating current) having a frequency and an amplitude for each peak or trough in the waveform. The waveform may also be described by an envelope or outline enveloping the amplitudes of the waveform such that in one example the amplitude of the envelope may increase and then decrease to zero or near zero at the end of the echo. In one or more embodiments, successive NMR measurements are performed with each NMR measurement having a slightly different magnitude of the pulsed magnetic field gradient from the magnitude of the previous NMR measurement. The first pulsed magnetic field gradient may be considered to encode the position of molecules in the sample while the second pulsed magnetic field may be considered to decode the position of the molecules to determine their amount of movement over a time interval relative to their encoded locations.

Figure 3:
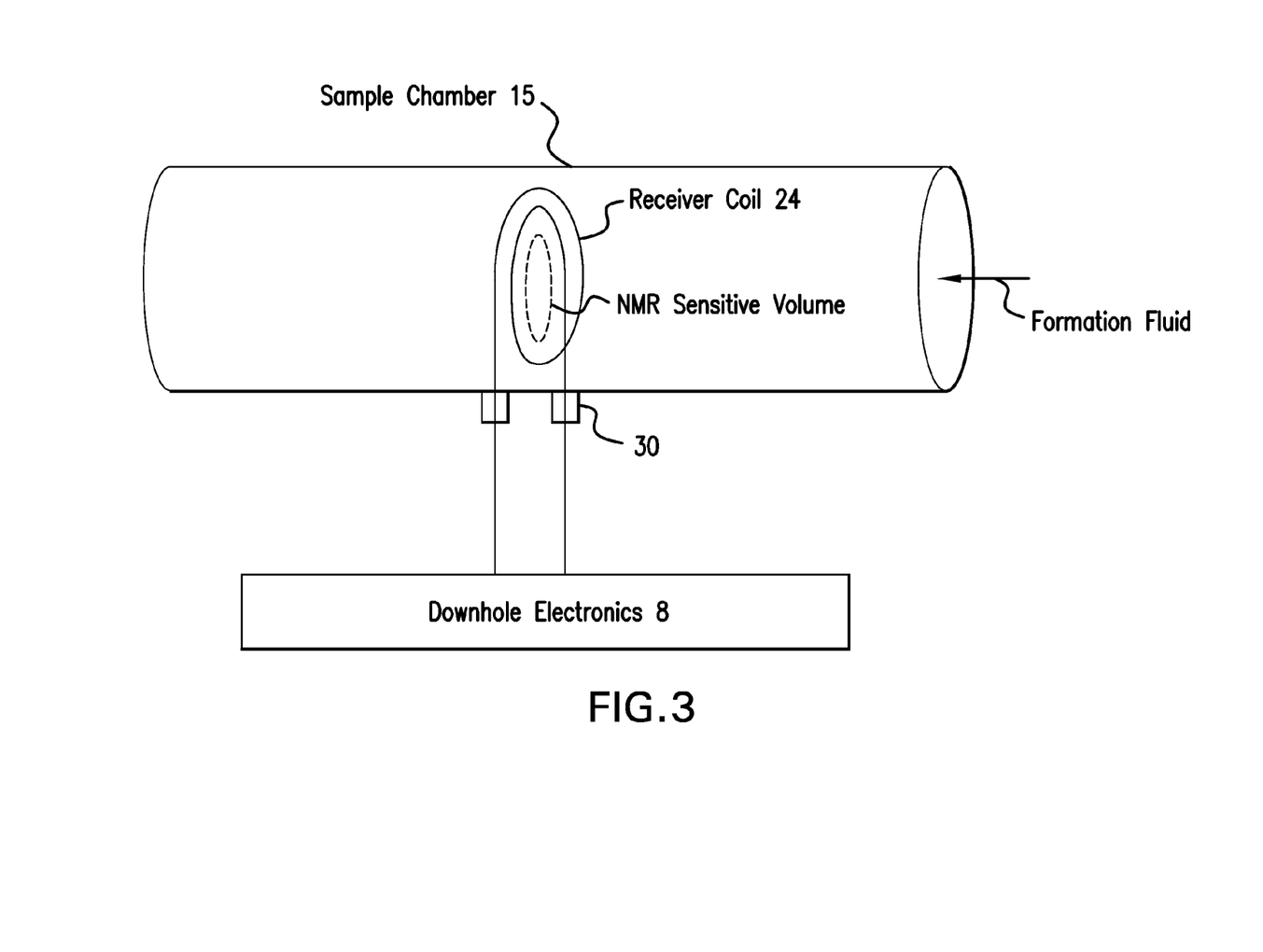
FIG. 3 depicts aspects of a receiver antenna disposed within a sample chamber and defining a sensitive volume within the sample chamber.

One way to achieve a homogeneous magnetic field is to decrease the size of the sensitive volume to the point where the magnitude of the field varies less than 5 ppm over that volume. One technique to decrease the sensitive volume is to decrease the size the receiver antenna 24. In the embodiment of the receiver antenna 24 as a coil, the coil may be a micro-coil fabricated as a micro-electrical-mechanical-system (MEMS) using semiconductor fabrication techniques. In general, a diameter of a micro-coil is less than or equal to 500 microns. The diameter of the micro-coil, in one or more embodiments, may be 350 microns or less, 150 microns or less, or 120 microns or less. The receiver coil 24 may be disposed in the sample chamber 15 as illustrated in FIG. 3. In the embodiment of FIG. 3, the sample chamber 15 includes electrical penetrations 30 for electrically connecting the receiver coil 24 to the downhole electronics 8. In another embodiment, the size of the sensitive volume may be decreased by using a capillary tube as the sample chamber 15 and wrapping the receiver coil 24 around the capillary tube. The bore diameter of the capillary tubing is generally less than 2 mm. It can be appreciated that another advantage to using a small sensitive volume is that the total space required for the NMR instrument components is reduced and can fit within the spatial requirements of the borehole.

Other techniques may be used to achieve a static homogeneous magnetic field. In one technique, the position of individual magnets in an array may be modulated to generate spherical harmonic corrections to the resulting magnetic field to provide increased homogeneity, but the modulating may also increase the complexity of the device. Alternatively, moving magnets farther away from the sensitive volume may increase the uniformity of the static magnetic field with the size of the downhole tool as required for conveyance in the borehole being a limiting factor along with decreased strength of the magnetic field in the sensitive volume.

The received echo may be processed in real time as it is received or it may be recorded for later processing. In one or more embodiments, processing may include transforming the received waveform into the frequency domain (where the transform is a function of frequency) to obtain the spectral content of the waveform. The spectral content may include amplitudes of peaks and the frequencies of those peaks. By changing the pulsed magnetic field gradient, the precession frequency of the proton magnetic moments or spins will change because the Larmor frequency of the proton magnetic moments is a function of the magnitude of the total magnetic field in the sensitive volume. Hence, the spectral content of the echo will also change according to the change in the magnitude of the pulsed magnetic field gradient. From the plurality of NMR measurements with each measurement at a different magnitude of the pulsed magnetic field gradient, an NMR resonant frequency for the sample can be determined such as by the frequency having the highest amplitude in the spectral content. Once, the NMR resonant frequency of the sample is obtained, that NMR resonant frequency can be compared to a reference frequency of a reference standard to provide a proton chemical-shift relative to the reference standard. The size, position, and number of proton chemical shifts are indicative of a structure of a molecule in the sample. Proton chemical-shift information for known materials (e.g., water) and hydrocarbons of interest can be obtained through laboratory or field NMR testing. Alternatively, the proton chemical shift information for known materials and hydrocarbons of interest can be obtained through analysis or in combination with testing. In addition, the specific configuration of the NMR instrument 10 can be calibrated for determining proton-chemical shift information in a laboratory using the known materials and hydrocarbons on interest.

It can be appreciated that any or several mathematical transforms may be used to transform the received echo waveform from the time domain into the frequency domain. In one or more embodiments, the Fourier transform may be used as this mathematical transform.

The NMR signals may also be used to determine a rate of diffusion, characterized by a diffusion constant, of molecules in the sample. Larger molecules will diffuse more slowly in the sample than smaller molecules and, thus, larger molecules will have a smaller diffusion constant than the diffusion constant of the smaller molecules (i.e., $D_{large\ molecules} < D_{small\ molecules}$). In an embodiment where two pulsed magnetic fields are applied to the sample, if the magnetic spins have not undergone any translational motion, the effects of the two applied field gradient pulses cancel and all spins refocus. However, if the magnetic spins have moved between the two magnetic field gradient pulses, the degree of dephasing due to the second applied field gradient pulse is proportional to the displacement in the direction of the first field gradient pulse in the time period between the leading edges of the two field gradient pulses. Hence, in one or more embodiments, the diffusion constant is directly related to the attenuation of the received waveform signal. In one or more embodiments, the Laplace transform of the frequency domain amplitudes as a function of the magnitude of the pulsed magnetic field gradient is used to quantify the attenuation the received waveform signal. It can be appreciated that other transforms or mathematical operations can also be used to quantify the attenuation of the received waveform signal. Correlations between quantification of attenuation of the received signal and the diffusion constant can be obtained through laboratory or field NMR testing using known materials (e.g., water) and hydrocarbons of interest. Alternatively, the correlations for known materials and hydrocarbons of interest can be obtained through analysis or in combination with testing. In addition, the specific configuration of the NMR instrument 10 can be calibrated for determining diffusion constants in a laboratory using the known materials and hydrocarbons on interest. Once the correlations are obtained, the attenuation quantification can be compared to the correlations to determine the diffusion constant of the sample.

Figure 4:
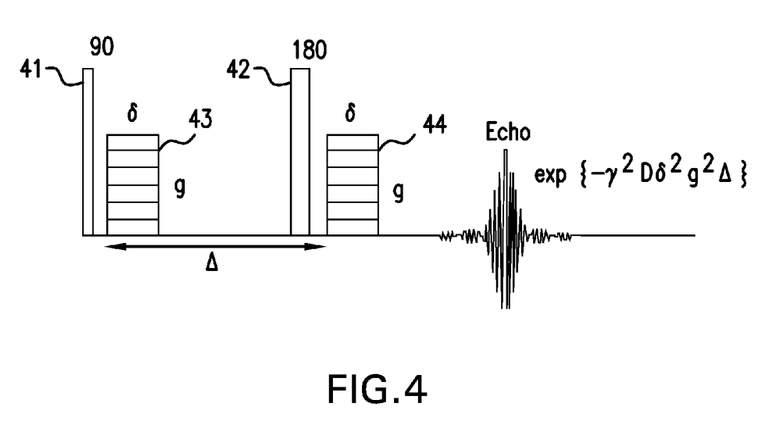
FIG. 4 depicts aspects of one example of a pulse field gradient spin-echo sequence.
Figure 5:
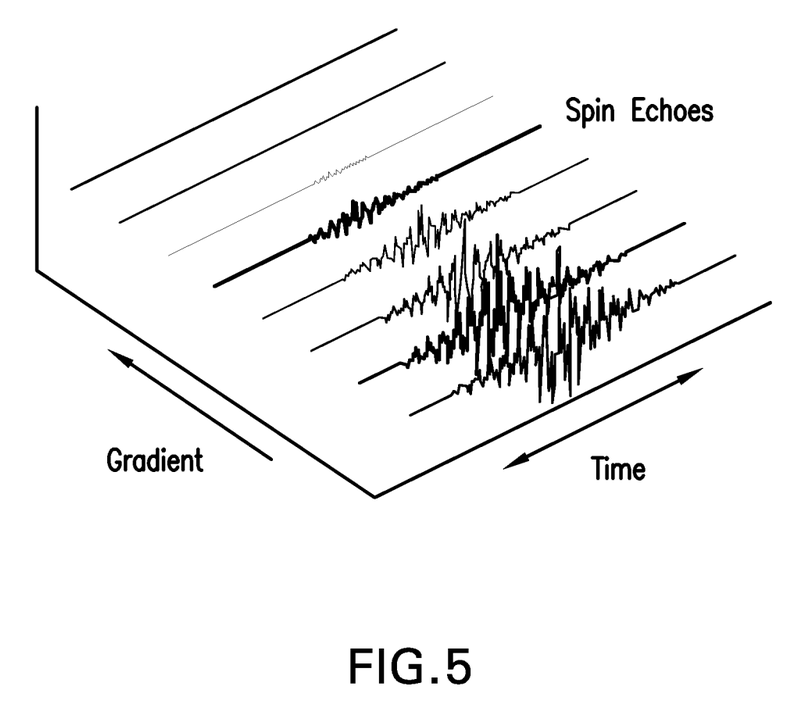
FIG. 5 depicts aspects of spin-echoes as a function of time and gradient.
Figure 6:
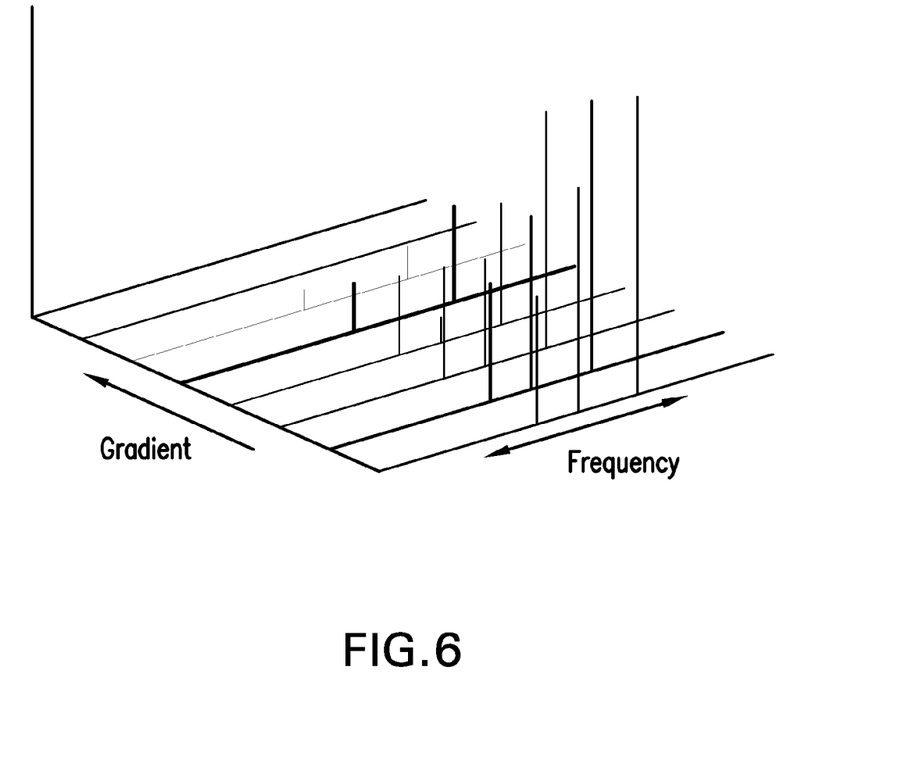
FIG. 6 depicts aspects of a Fourier transform of each of the spin-echoes.
Figure 7:
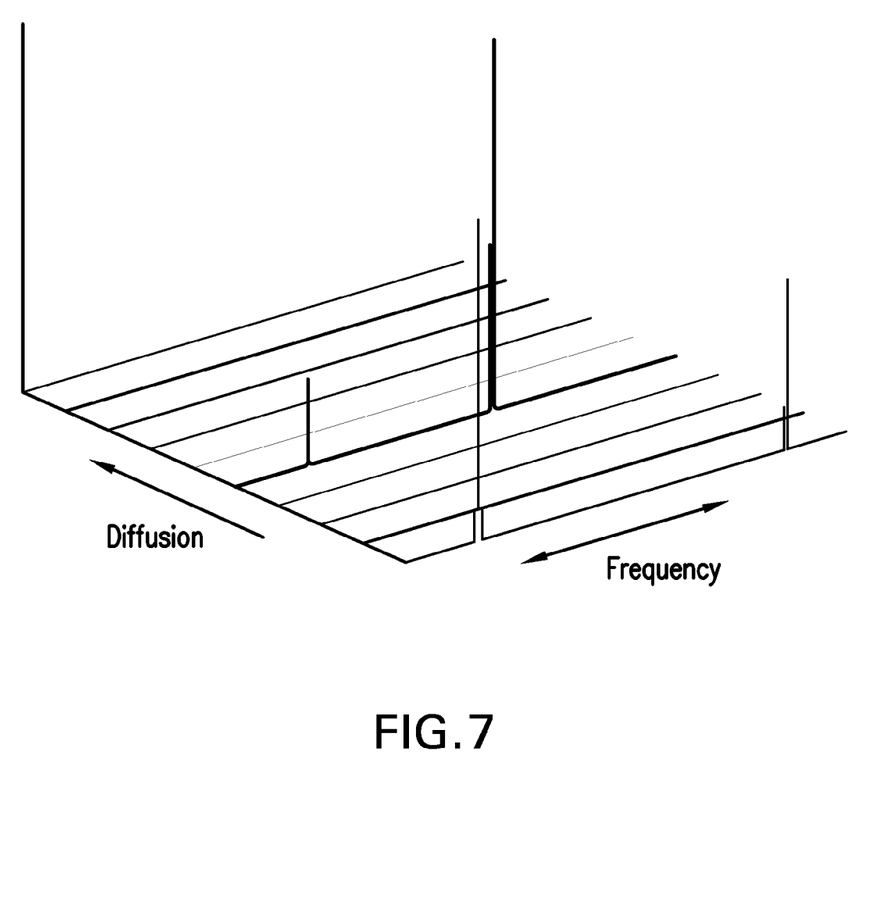
FIG. 7 depicts aspects of a Laplace transform applied to Fourier transform in the gradient direction.

For teaching or operational purposes, the techniques discussed above may be graphically presented. The spin echo waveform may be graphed as signal (e.g., voltage) amplitude (y-axis) versus time (x-axis). FIG. 4 illustrates one example of a pulsed field gradient spin-echo sequence. Boxes 41 and 42 represent the application of the RF magnetic field pulses. The first RF pulse (box 41) excites the nuclear spin to create a signal. That signal decays away and is not shown. The second RF pulse (box 42) reverses the signal decay and generates the spin-echo. Boxes 43 and 44 represent the application of the pulsed magnetic field gradient to the nuclear spins. The first pulsed magnetic field gradient (box 43) encodes the position of the nuclear spins, while the second pulsed magnetic field gradient (box 44) decodes the position. If the nuclear spins have not moved, the spin-echo signal is not attenuated. The average attenuation is given by the expression in FIG. 4 where gamma is the gyromagnetic moment of the nuclear spins, D is the molecular diffusion constant, g is the amplitude of the pulsed magnetic field gradient, δ is the length of time of the gradient pulse, and Δ is the time between the gradient pulses. Other pulse sequences such as a stimulated pulse sequence and sequences with bipolar gradients are also possible. FIG. 5 illustrates one example of spin-echo signals (or waveforms) as a function of time and pulsed magnetic field gradient. The Fourier transform of the FID waveform may be graphed as amplitude of the Fourier transform values (y-axis) versus frequency (x-axis). Because each NMR measurement has a different magnitude of the pulsed magnetic field gradient, each Fourier transform can be plotted as a function of pulsed field gradient magnitude (z-axis) for a three-dimensional graph. FIG. 6 illustrates one example of a Fourier transform of each spin-echo signal. The Laplace transform or another suitable inversion technique is then applied to each vertical slice in the y-z plane (i.e., with frequency being constant for each Laplace transform). In other words, the Laplace transform is applied to Fourier transform amplitudes at the same frequency as a function of the pulsed field gradient amplitude. The Fourier transform data provides the proton-chemical shift information and the Laplace transform data provides diffusion constants of the molecules in the sample. FIG. 7 illustrates one example of a Laplace transform of the frequency domain amplitudes in the gradient direction. In the gradient direction, the amplitudes have the same frequency. After the Laplace transform, the molecular species NMR spectra are distinct and the diffusion of each species is related to its molecular size.

Each data type (Fourier transform versus Laplace transform) itself may not be sufficient to completely characterize the molecules in the sample. For example, a first hydrocarbon molecule may include one benzene ring while a second hydrocarbon molecule may include two benzene rings with the second hydrocarbon molecule being larger than the first hydrocarbon molecule because of the second benzene ring. The proton chemical-shift information for the two molecules may be similar or the same due to the benzene ring or rings. However, the first hydrocarbon molecule will have a diffusion constant that is greater than the diffusion constant of the second hydrocarbon molecule due to the first hydrocarbon molecule being smaller than the second hydrocarbon molecule. Hence, the combination of the two types of data can distinguish between the two different types of molecules and identify each of them. Accordingly, the two data types may be presented as a matrix of data points where each data point includes the determined proton chemical-shift information and diffusion constant.

Hydrocarbons in formations may be composed of different functional groups such as saturates, aromatics, resins, and asphaltenes. It may be desirable to estimate the fraction of these different functional groups in the sample as well as estimate the fraction of the different types of hydrocarbons such as C1 (methane), C2, (ethane), C3, (butane), C4, C5, etc. In saturated hydrocarbons, every carbon atom is attached to two hydrogen atoms, except those at the ends of the chain, which bear three hydrogen atoms. In the case of saturated ethane, each carbon center has four single bonds as is characteristic of other saturated hydrocarbons. In contrast, in ethylene ($C_2H_4$), each carbon center is engaged in two single and one double bond. An aromatic hydrocarbon is a hydrocarbon with alternating double and single bonds between carbon atoms forming rings. The configuration of six carbon atoms in aromatic compounds is known as a benzene ring, after the simplest possible such hydrocarbon, benzene. Asphaltenes consist primarily of carbon, hydrogen, nitrogen, oxygen, and sulfur, as well as trace amounts of vanadium and nickel. The C:H ratio is approximately 1:1.2, depending on the asphaltene source. Asphaltenes are defined operationally as the n-heptane ($C_7H_{16}$)-insoluble, toluene ($C_6H_5CH_3$)-soluble component of crude oil. A distribution of molecular masses of asphaltenes have been shown to be in the range of 400 u to 1500 u, with an average being around 750 u. Hence, by identifying the various different types of hydrocarbons and their fraction in the sample, the fraction of the different function groups in the sample may also be estimated.

Figure 8:
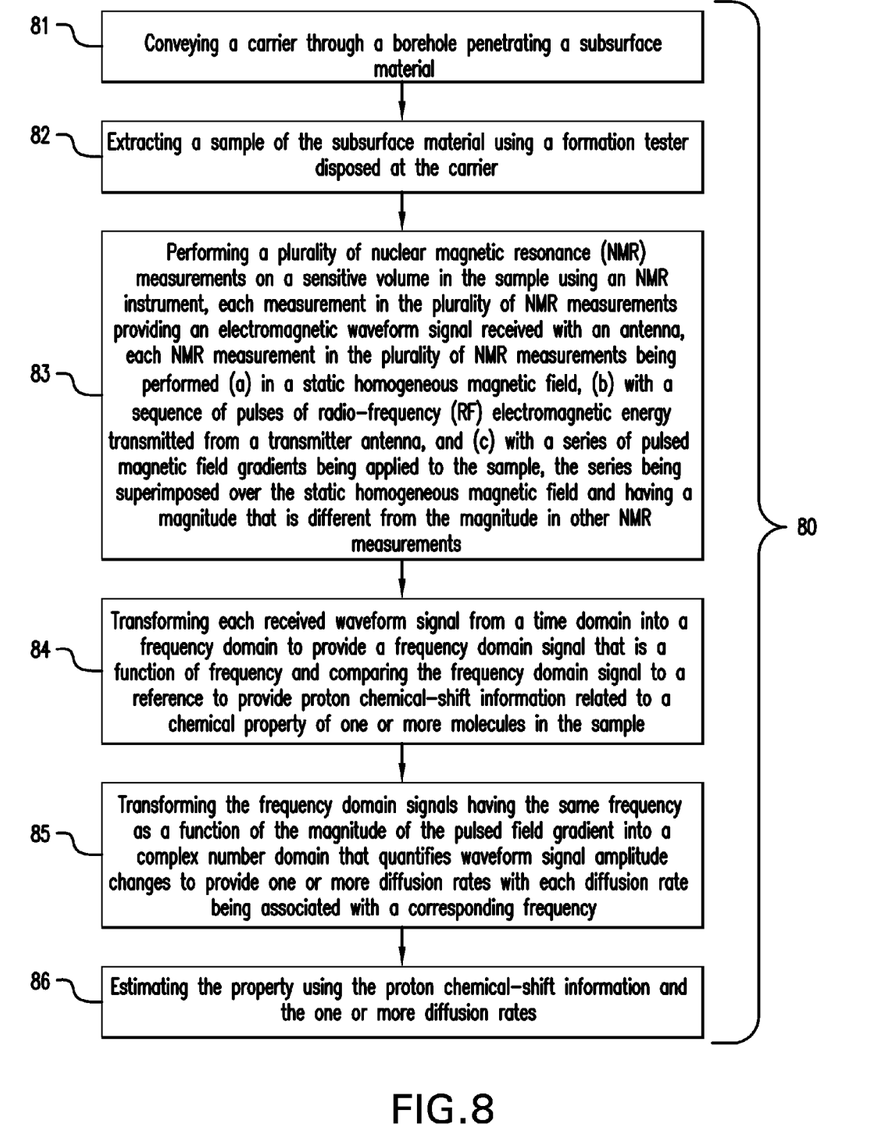
FIG. 8 is a flow chart for a method for estimating a property of an earth formation material.

FIG. 8 presents a flow chart for a method 80 for estimating a property of a subsurface material. Block 81 calls for conveying a carrier through a borehole penetrating the subsurface material. Block 82 calls for extracting a sample of the subsurface material using a formation tester disposed at the carrier. Block 83 calls for performing a plurality of nuclear magnetic resonance (NMR) measurements on a sensitive volume in the sample using an NMR instrument, each measurement in the plurality of NMR measurements providing an electromagnetic waveform signal received with an antenna and each NMR measurement in the plurality of NMR measurements being performed in a static homogeneous magnetic field. Further, each measurement in the plurality of NMR measurements is performed with a sequence of pulses of radio-frequency (RF) electromagnetic energy transmitted from a transmitter antenna and with a series of pulsed magnetic field gradients being applied to the sample where each pulsed magnetic field gradient is superimposed over the static homogeneous magnetic field and has a magnitude that is different from the magnitude in other measurements. In one or more embodiments, each pulsed magnetic field gradient is applied to the sample after each RF pulse. In other embodiments, each pulsed magnetic field gradient is applied in another order. Block 84 calls for transforming each received waveform signal from a time domain into a frequency domain to provide a frequency domain signal that is a function of frequency and comparing the frequency domain signal to a reference to provide proton chemical-shift information related to a chemical property of one or more molecules in the sample. Block 85 calls for transforming the frequency domain signals having the same frequency as a function of the magnitude of the pulsed field gradient into a complex number domain that quantifies waveform signal amplitude changes to provide one or more diffusion rates with each diffusion rate being associated with a corresponding frequency. A diffusion rate may be characterized by a diffusion constant where a higher rate of diffusion is quantified by a higher diffusion constant. Block 86 calls for estimating the property using the proton chemical-shift information and the one or more diffusion rates. The property may relate to identifying one or more types of molecules and a distribution of the one or more types of molecules.

It can be appreciated that one or more advantages to using a homogeneous static magnetic field relate to increasing the accuracy and precision of NMR measurements necessary for identifying different chemical structures of molecules that may have similar structures and for quantifying a distribution of various molecules in the sample and, thus, the formation.

In support of the teachings herein, various analysis components may be used, including a digital and/or an analog system. For example, the downhole electronics 8, the computer processing system 9, or the downhole tool 10 may include digital and/or analog systems. The system may have components such as a processor, storage media, memory, input, output, communications link (wired, wireless, pulsed mud, optical or other), user interfaces, software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of computer executable instructions stored on a non-transitory computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

The term "carrier" as used herein means any device, device component, combination of devices, media and/or member that may be used to convey, house, support or otherwise facilitate the use of another device, device component, combination of devices, media and/or member. Other exemplary non-limiting carriers include drill strings of the coiled tube type, of the jointed pipe type and any combination or portion thereof. Other carrier examples include casing pipes, wirelines, wireline sondes, slickline sondes, drop shots, bottom-hole-assemblies, drill string inserts, modules, internal housings and substrate portions thereof.

Elements of the embodiments have been introduced with either the articles "a" or "an." The articles are intended to mean that there are one or more of the elements. The terms "including" and "having" are intended to be inclusive such that there may be additional elements other than the elements listed. The conjunction "or" when used with a list of at least two terms is intended to mean any term or combination of terms. The terms "first" and "second" are used to distinguish elements and do not denote a particular order. The term "coupled" relates to a first component being coupled either directly to a second component or indirectly through an intermediate component.

It will be recognized that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood that various changes may be made and equivalents may be substituted for elements thereof without departing from the scope of the invention. In addition, many modifications will be appreciated to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for estimating a property of subsurface material, the method comprising:
   conveying a carrier through a borehole penetrating the subsurface material;
   extracting a sample of the subsurface material using a formation tester disposed at the carrier;
   performing a plurality of nuclear magnetic resonance (NMR) measurements on a sensitive volume in the sample using an NMR instrument, each measurement in the plurality of NMR measurements providing an electromagnetic waveform signal received with an antenna, each NMR measurement in the plurality of NMR measurements being performed (a) in a static homogeneous magnetic field, (b) with a sequence of pulses of radio-frequency (RF) electromagnetic energy transmitted from a transmitter antenna, and (c) with a series of pulsed magnetic field gradients being applied to the sample, the series of pulsed magnetic field gradients being superimposed over the static homogeneous magnetic field and the series of pulsed magnetic field gradients having a magnitude that is different from the magnitude of the series of pulsed magnetic field gradients in other NMR measurements;
   transforming each received waveform signal from a time domain into a frequency domain to provide a frequency domain signal that is a function of frequency and comparing the frequency domain signal to a reference to provide proton chemical-shift information related to a chemical property of one or more molecules in the sample;
   transforming the frequency domain signals having the same frequency as a function of the magnitude of the pulsed field gradient into a complex number domain that quantifies waveform signal amplitude changes to provide one or more diffusion rates with each diffusion rate being associated with a corresponding frequency; and
   estimating the property using the proton chemical-shift information and the one or more diffusion rates.

2. The method according to claim 1, further comprising relating the proton chemical-shift information to one or more chemical properties of one or more molecules.

3. The method according to claim 2, further comprising relating the diffusion rates to a size of the one or more molecules.

4. The method according to claim 1, wherein transforming each received waveform signal from a time domain into a frequency domain comprises using a Fourier transform.

5. The method according to claim 1, wherein transforming the frequency domain signals comprises using a Laplace transform.

6. The method according to claim 1, wherein the homogeneous magnetic field varies by less than 5 parts per million over the sensitive volume.

7. The method according to claim 1, wherein a diameter of the sensitive volume is 500 microns or less.

8. The method according to claim 1, wherein the property is a quantification of a distribution of one or more molecules in the sample.

9. The method according to claim 1, further comprising identifying the subsurface material as at least one selection from a group consisting of saturates, aromatics, resins, and asphaltenes.

10. An apparatus for estimating a property of a subsurface material, the apparatus comprising:
    a carrier configured to be conveyed through a borehole penetrating the subsurface material;
    a formation tester disposed at the carrier and configured to extract a sample of the subsurface material;
    a nuclear magnetic resonance (NMR) instrument disposed at the carrier and configured to perform a plurality of nuclear magnetic resonance (NMR) measurements on a sensitive volume in the sample, each measurement in the plurality of NMR measurements providing an electromagnetic waveform signal, each NMR measurement in the plurality of NMR measurements being performed (a) in a static homogeneous magnetic field, (b) with a sequence of pulses of radio-frequency (RF) electromagnetic energy transmitted from a transmitter antenna, and (c) with a series of pulsed magnetic field gradients being applied to the sample, the series of pulsed magnetic field gradients being superimposed over the static homogeneous magnetic field and the series of pulsed magnetic field gradients having a magnitude that is different from the magnitude of the series of pulsed magnetic field gradients in other NMR measurements, the NMR instrument comprising:
      a magnetic field source configured to apply the homogeneous magnetic field to the sensitive volume;
      a transmitter antenna configured to transmit a radio-frequency (RF) signal into the sensitive volume;

a pulsed magnetic field gradient source configured to apply the series of pulsed magnetic field gradients with various magnitudes to the sensitive volume;

a receiver antenna configured to receive the electromagnetic waveform signals from the sensitive volume due the RF signal and the pulsed magnetic field gradient; and a processor configured to:

receive each of the electromagnetic waveform signals;

transform each received waveform signal from a time domain into a frequency domain to provide a plurality of frequency domain signals and compare the frequency domain signals to a reference to provide proton chemical-shift information related to a chemical structure of one or more molecules in the sample;

transform the frequency domain signals at the same frequency as a function of the magnitude of the pulsed field gradient into a complex number domain that quantifies waveform signal amplitude changes to provide one or more diffusion rates with each diffusion rate being associated with a corresponding frequency; and estimate the property using the proton chemical-shift information and the one or more diffusion rates.

11. The apparatus according to claim 10, further comprising a sample tube configured to contain the sample for the NMR measurements.

12. The apparatus according to claim 11, wherein the magnetic field source comprises a Halbach array of magnets surrounding the sample tube, the array being configured to apply the homogeneous magnetic field to the sensitive volume.

13. The apparatus according to claim 11, wherein the receiver antenna is a coil disposed inside of the sample tube and surrounds the sensitive volume.

14. The apparatus according to claim 13, wherein the sample tube comprises an electrical penetration coupled to the coil.

15. The apparatus according to claim 13, wherein the coil is a micro-coil fabricated as a micro-electrical-mechanical-system (MEMS) and having a diameter of 500 microns or less.

16. The apparatus according to claim 11, wherein the sample container is a capillary tube.

17. The apparatus according to claim 15, wherein the magnetic field source is a coil surrounding the capillary tube.

18. The apparatus according to claim 10, wherein the pulsed magnetic field gradient source comprises a coil magnetically coupled to the sensitive volume.

* * * * *